United States Patent
Colvin

(10) Patent No.: US 6,245,586 B1
(45) Date of Patent: Jun. 12, 2001

(54) WIRE-TO-WIRE BONDING SYSTEM AND METHOD

(76) Inventor: James Barry Colvin, 36217 Worthing Dr., Newark, CA (US) 94560

(*) Notice: Subject to any disclaimer, the term of this patent is extended or adjusted under 35 U.S.C. 154(b) by 0 days.

(21) Appl. No.: 09/415,517

(22) Filed: Oct. 7, 1999

Related U.S. Application Data

(60) Provisional application No. 60/103,593, filed on Oct. 9, 1998.

(51) Int. Cl.$^7$ ................................................... H01L 21/66
(52) U.S. Cl. ............................... 438/15; 438/12; 438/14; 216/21
(58) Field of Search .................................. 438/12, 14, 15, 438/17, 115; 216/21

(56) References Cited

U.S. PATENT DOCUMENTS

| | | | | |
|---|---|---|---|---|
| 5,326,709 | * | 7/1994 | Moon et al. ............................. | 438/12 |
| 5,391,501 | * | 2/1995 | Ugami et al. ........................... | 438/12 |
| 5,698,474 | | 12/1997 | Hurley . | |
| 5,707,411 | * | 1/1998 | Rudaway et al. ....................... | 55/496 |
| 5,904,489 | * | 5/1999 | Khoropour et al. ................... | 438/15 |
| 5,926,688 | * | 7/1999 | Lee et al. ................................ | 438/17 |
| 6,043,100 | * | 3/2000 | Weaver et al. ......................... | 438/15 |
| 6,096,568 | * | 8/2000 | Dobrovolski .......................... | 438/15 |

OTHER PUBLICATIONS

"Leadframe"; http://www.shinko.co.jp/products/e_lead.htm; 2 pages; Not dated.
"Integrated Circuit Packaging"; Electronics Industry Environmental Roadmap: Integrated Circuit Packaging; http://www.mcc.com/env/roadmap/roadmap.pack.html; 5 pages; Not dated.

* cited by examiner

*Primary Examiner*—Kevin M. Picardat
(74) *Attorney, Agent, or Firm*—Smith, Danamraj & Youst, P.C.

(57) ABSTRACT

A system and method for preparing semiconductor samples for analytical techniques such as backside emission microscopy. Samples may be prepared from a wafer or packaged die. In package form, the package is affixed to a polishing jig such that the backside of the die is oriented to face a polishing wheel. The package material is removed until die attach paddle and the backside of the die are exposed. The material is further removed until a selected thinness of the die is obtained. If the package's leadframe or a portion thereof remains after the removal of package material, a suitable testing fixture is attached thereto. If the leadframe is sacrificed, wire spots on the polished side of the semiconductor die are wire-to-wire bonded to a second leadframe's conductive fingers. In wafer form, the die is separated and encapsulated with a suitable substantially rigid material to form a substantially rigid body that is affixed to the polishing jig.

40 Claims, 8 Drawing Sheets

WIRE-TO-WIRE BONDING SYSTEM AND METHOD

PRIORITY UNDER 35 U.S.C. §119(e) & 37 C.F.R. §1.78(a)

This nonprovisional application claims priority based upon the following prior U.S. Provisional Patent Application entitled "Backside Package Wire to Wire Bonding," Ser. No. 60/103,593, filed Oct. 9, 1998, in the name of James Barry Colvin.

CROSS-REFERENCE TO RELATED APPLICATIONS

This nonprovisional application discloses subject matter that is related to the subject matter disclosed in the following patent applications: (i) "Emission Microscopy System," Ser. No. 09/181,117 (filed Oct. 28, 1998), in the name of James Barry Colvin; (ii) "Coherent Illumination System and Method," Ser. No. 09/181,261 (filing date of Oct. 28, 1998), in the name of James Barry Colvin.

BACKGROUND OF THE INVENTION

1. Technical Field of the Invention

The present invention relates generally to the field of failure analysis, packaging, and assembly techniques employed in the manufacture and testing of semiconductors. More particularly, and not by way of any limitation, the present invention is directed to a wire-to-wire bonding system and method that provides semiconductor samples for such analytical techniques as backside emission microscopy. In addition, the present invention is also directed to providing stackable semiconductor devices for multi-chip assembly.

2. Description of Related Art

Light (or photon) emission microscopy is a common failure analysis (FA) technique used for analyzing semiconductor integrated circuit (IC) devices. The considerations involved in using photon emission to successfully analyze defects and failure mechanisms in CMOS ICs are well known. IC failure analysis using an emission microscope is performed by collecting visible (390–770 nm), and near infrared (NIR) (770–1000 nm, with the typical IR band defined as 770–1500 nm), wavelength photons emitted from transistors, p/n junctions, and other photon-generating structures on or near the top (front), electrically-active, silicon surface. These photons are transmitted through the overlying, relatively transparent dielectric layers, passing between or scattered around the patterned, opaque metal interconnections. Detection of photons that emerge from around these overlying layers is referred to as frontside light emission analysis. Correspondingly, imaging light passing through the silicon substrate and emerging from the bottom (back) is referred to as backside light emission analysis.

There is an increasing interest in backside light emission analysis. This is driven, at least in part, by the advancement of IC fabrication technologies with additional opaque conductor layers and packaging technologies that typically obscure the active side (i.e., the front side) of the die. Backside analysis takes advantage of silicon's transmission of photons with energies less than its indirect silicon bandgap energy, corresponding to wavelengths greater than around 1.107 $\mu$m (for undoped silicon). It is commonly known that silicon becomes less transparent as dopants are added. Because of this phenomenon, the heavily doped substrates often used with newer technologies will attenuate NIR light emitted from the active circuits. These and other factors are stimulating research for solutions, including improved substrate thinning techniques, increased NIR imaging sensitivity, and sophisticated spectral analysis.

It is well known that different types of photon emission processes can be distinguished by their spectra. Photon emission from defects or abnormal operation of silicon microelectronic devices generally falls into the following categories: forward or reverse biased p/n junctions, transistors in saturation, latchup, and gate oxide breakdown. While radiative recombination emission from silicon structures is generally centered around 1.1 $\mu$m, commonly used cameras have spectral response centered in the 400–900 nm range and can thus capture only a small portion of the emitted light.

Traditional backside emission microscopy typically requires polishing of the die from the backside and socketing the resultant unit (i.e., die sample) in special fixturing for inspection with NIR energies through the polished silicon substrate. Sample preparation for backside analysis requires the sample to remain in the original package or wafer and be imaged through the bottom of the socket that makes electrical contact to the integrated circuit.

Currently, the methods for imaging with a charge-coupled device (CCD) camera involve time integration to acquire enough light to form an image of the circuitry under examination. Real-time IR imaging from the polished backside of a silicon-based IC is difficult due to low frame rates coupled with inadequate illumination intensity. Traditional methods of NIR imaging use an optical filter in conjunction with a broad-spectrum illuminator such as a quartz halogen bulb. The desired wavelengths pass through the filter and are used in the microscope illuminating path. The desired wavelength is selected by the filter when the unwanted light frequencies are rejected. One of the problems of the current technologies is that when a more intense illumination source is used to address at least in part the issue of the poor quantum efficiency of backside emission, the optical filters get degraded or destroyed quickly due to heating. The problem is further compounded by the fact that as the filter bandwidth is narrowed, the total energy is also reduced from the source output. On the other hand, employing longer integration times, by taking the emitted light inputs over a considerable period of time, negatively impacts the throughput. Due to these constraints, it can be appreciated that the current illumination technology cannot provide intense, narrow bandwidth illumination that is advantageous in backside emission analysis.

Laser sources can provide very intense, substantially monochromatic illumination. When these sources are used in backside emission analysis, however, interference phenomena cause what is commonly known as laser "speckle" that blur the illuminated image. The speckle is seen at least in part due to the nonuniform distribution of radiation energy, giving rise to "hot spots" and "dark areas". While techniques such as diffusing the laser light using a frosted glass, dithering (i.e., scanning the laser beam), et cetera, are sometimes used, they have not been sufficiently effective in alleviating the speckle problem in backside emission imaging. Further, it may be appreciated that the intensity of the light with which the sample is imaged is compromised in such methods. In addition, the recent popularity of Flip Chip technologies, escalation in the number of metal interconnect layers and advanced packaging techniques (for example, Ball Grid Arrays (BGAs), Land Grid Arrays (LGAs), etc.)— all of which obscure the front side view of the active area—justify analysis from the backside.

The following pending U.S. applications, currently owned by the inventor of the present patent application, disclose subject matter related to providing solutions to the aforesaid problems of the current illumination systems with respect to, for example, such FA techniques as backside emission microscopy: (i) "Emission Microscopy System," Ser. No. 09/181,117 (filed Oct. 28, 1998), in the name of James Barry Colvin; (ii) "Coherent Illumination System and Method," Ser. No. 09/181,261 (filed Oct. 28, 1998), in the name of James Barry Colvin.

Regardless of the imaging schemes and advances therein, the current technology of sample preparation for backside emission analysis is beset with various drawbacks and deficiencies. As alluded to in the foregoing, current sample preparation techniques for backside analysis require the sample to remain in the original package or wafer and be imaged through the bottom of the socket that makes electrical contact to the integrated circuit. However, certain advanced types of-packages, e.g., BGA packages, Chip-Scale Packages (CSPs), etc. cannot be effectively prepared for backside imaging using the traditional methods. In addition, the height of the socket and corresponding circuit board inhibit imaging at high magnification or with high numeric aperture (NA) due to the recessed "pocket" or "well" created pursuant to the socket dimensions. Also, it is well known that using high NA or employing macro lenses with such socket configurations results in beam vignetting as well, which, in turn, gives rise to undesirable effects in imaging. It should further be appreciated that because of the high profile of the socket well, short working distance objectives such as immersion lenses cannot be used across the die surface.

Furthermore, not only is the current backside sample preparation equipment costly, but also the existing equipment does not produce a flat backside surface after polishing, thereby giving rise to what is known as a "lens" effect through the silicon curvature.

Moreover, it is commonly known that there is a well-defined relationship between the silicon filter effect and thinning of the sample (i.e., how thick/thin the die is after polishing). Essentially, thinning the sample translates to increased emission sensitivity as well as improved optical resolution of the circuitry. Whereas several thinning techniques exist (for example, U.S. Pat. No. 5,698,474 to Hurley discloses a high speed diamond-based machining technique), the extant sample preparation technology, however, does not produce thin enough die samples suitable for producing optimal emission sensitivities and improved optical resolutions.

Based upon the forgoing, it should be realized that there has arisen an acute need for a solution that addresses these and other deficiencies and shortcomings of the current sample preparation technologies as set forth above. The present invention provides such a solution.

SUMMARY OF THE INVENTION

Accordingly, the present invention advantageously provides a system and method for preparing semiconductor samples for analytical techniques such as backside emission microscopy. Samples may be prepared from a wafer or packaged die. In package form, the package is affixed to a polishing jig such that the backside of the die is oriented to face a polishing wheel. The package material is removed until die attach paddle and the backside of the die are exposed. The material is further removed until a selected thinness of the die is obtained. If the package's leadframe or a portion thereof remains after the removal of package material, a suitable testing fixture is attached thereto. If the leadframe is sacrificed, wire spots on the polished side of the semiconductor die are wire-to-wire bonded to a second leadframe's conductive fingers. In wafer form, the die is separated and encapsulated with a suitable substantially rigid material to form a substantially rigid body that is affixed to the polishing jig.

In one aspect, the present invention is directed to method of preparing a semiconductor sample from a semiconductor die disposed in a package having a cavity bounded by a top and a bottom. The semiconductor die is attached to a leadframe through a die paddle and a plurality of wires bonded therebetween. If the package is of the open cavity type or the soft cavity type, the cavity is filled with a substantially rigid material such as a room temperature epoxy. Otherwise, if the package already contains encapsulating material, the package is used as such for sample preparation. The package is affixed to a polishing jig such that the die's backside is oriented to face a polishing wheel. The package material is removed starting from the bottom of the package, including the substantially rigid material. The material is removed until the die attach paddle and the backside of the semiconductor die are exposed. Additional material is removed until a selected thickness of the die is obtained.

If the leadframe is sacrificed in the process of material removal, the thinned die in the package is placed in a second package with a wireframe having a plurality of lead fingers. The exposed wire spots on the backside of the thinned die are wire-to-wire bonded to the plurality of lead fingers. If the leadframe is not sacrificed, a suitable fixture such as a probe-card may be used to probe the leadframe. Or, in an alternative embodiment, a wireframe may be bonded to the leadframe.

In further aspect, the present invention relates to a method of sample preparation from a die in wafer form. The die is separated out and attached to a leadframe through the die attach paddle and a plurality of wires. An encapsulating material is applied over the attached die to form a substantially rigid body. Thereafter, the body is affixed to a polishing jig such that the backside of the die is oriented to face a polishing wheel. Steps substantially similar to those set forth above are then implemented to obtain a sample.

BRIEF DESCRIPTION OF THE DRAWINGS

A more complete understanding of the present invention may be had by reference to the following Detailed Description when taken in conjunction with the accompanying drawings wherein.

DETAILED DESCRIPTION OF THE DRAWINGS

Figure 1A:
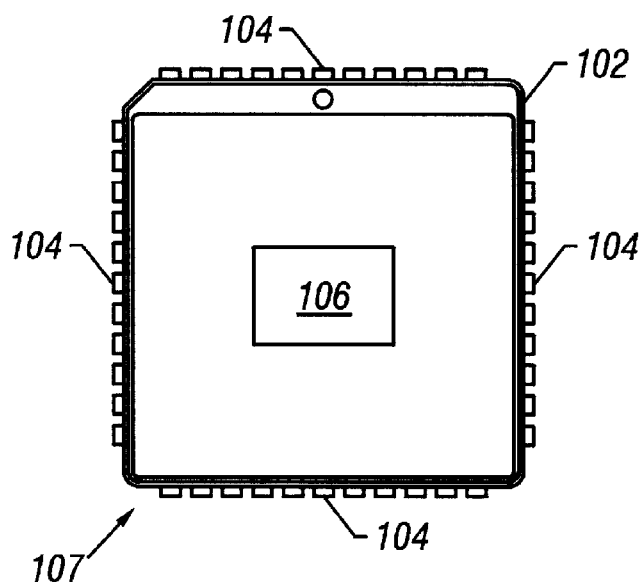
FIG. 1A depicts an exemplary package having a semiconductor die therein for practicing the teachings of the present invention.

In the drawings, like or similar elements are designated with identical reference numerals throughout the several views, and the various elements depicted are not necessarily drawn to scale. Referring now to FIG. 1A, depicted therein is an exemplary package 107 wherein a semiconductor die 106 is conventionally disposed therein. A plurality of leads 104 attached to a leadframe (not shown) emerge from the package 107 along its sides near the bottom 102.

The package 107 may be of the open cavity type (e.g., ceramic) or soft cavity type (such as with a die coat), in addition to other numerous variations wherein the cavity of the package is provided with a substantially rigid material such as an epoxy that encapsulates the semiconductor die 106 along with the leadframe and the wires attached therebetween. As will be described in further detail hereinbelow, the present invention's sample preparation technique calls for removing the package material from the bottom 102 of the package including the encapsulating material. If the die 106 is not already encapsulated, the presently preferred exemplary embodiment of the present invention involves filling the cavity with a suitable material for such purpose.

Figure 1B:
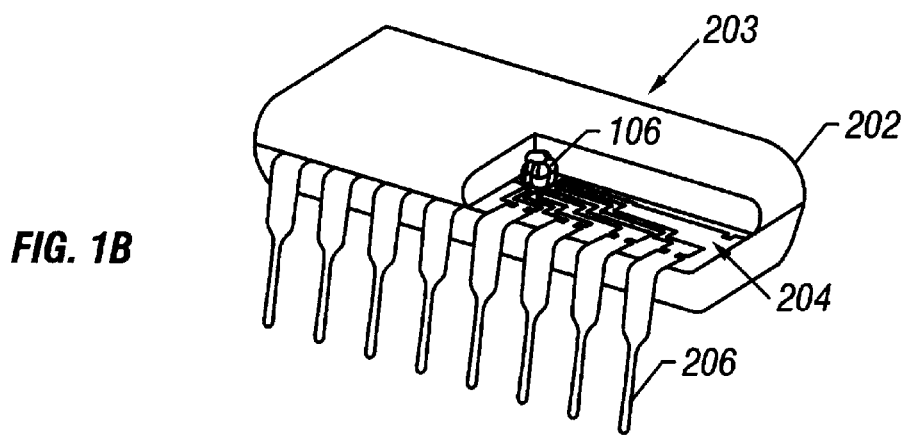
FIG. 1B depicts another exemplary package having a semiconductor die therein for practicing the teachings of the present invention.
Figure 1C:
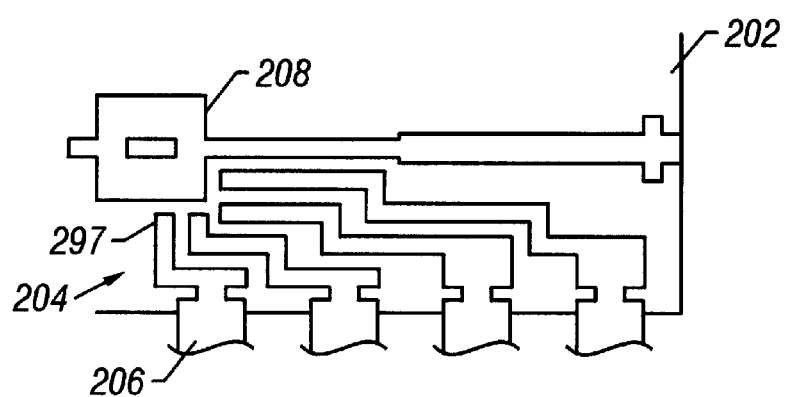
FIG. 1C depicts an exemplary leadframe arrangement for use with packages such as those shown in FIGS. 1A and 1B.

FIG. 1B depicts another exemplary package 203 having a semiconductor die (e.g., die 106) therein. The package 203 preferably comprises a plastic body 202 which encases the die 106 that is attached to a leadframe 204. A plurality of leads 206 are exemplified. FIG. 1C depicts additional details of an exemplary leadframe (e.g, leadframe 204) which may be provided in such packages as, for example, the packages 107 or 203. A die paddle 208 is provided for die attachment. After attaching the semiconductor die 106 to the die paddle 208, the bond pads (not shown) of the die are wire-bonded to lead fingers (e.g., lead finger 297) of the leadframe 204.

Figure 2A:
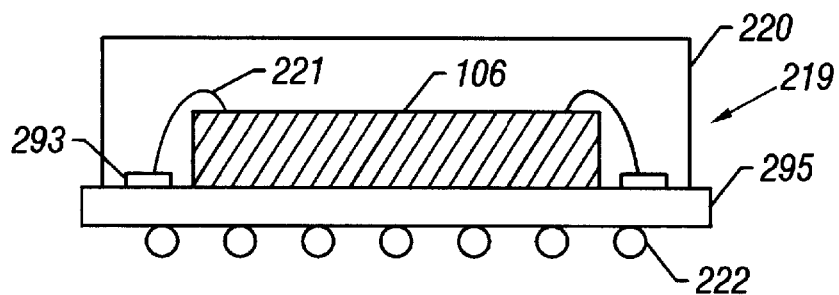
FIG. 2A depicts an exemplary BGA package for practicing the teachings of the present invention.

Referring now to FIG. 2A, an exemplary BGA package 219 is shown therein. A single die (e.g., die 106) is disposed in an encapsulating mold 220 on a first surface of a substrate 295. A plurality of conductive balls, e.g., solder balls 222, are provided on a second surface (preferably the opposite surface of the first surface where the mold 220 is provided) of the substrate 295 for establishing electrical connectivity. Wires (e.g., wire 221) are provided between the die 106 and conductive posts (e.g., post 293) which are disposed in an electrical conductive relationship with the solder balls 222.

Figure 2B:
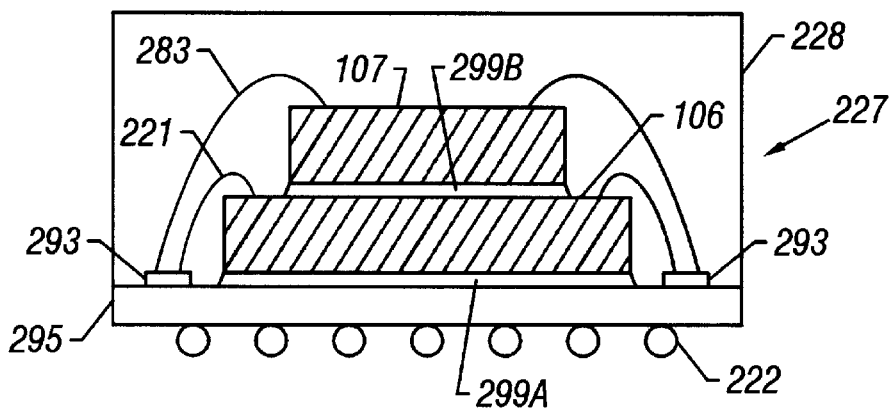
FIG. 2B depicts an exemplary CSP module for practicing the teachings of the present invention.

Referring to FIG. 2B, an exemplary CSP arrangement 227 having stacked semiconductor chips therein is shown. The semiconductor die 106 is attached to the substrate 295 using a die attach paste layer 299A. Another chip 107, which may comprise a functionality different from that of the die 106, is attached to the die 106 with a suitable arrangement, for example, a die attach layer 299B. Each of the chips is electrically coupled via wires (e.g., wire 221 or wire 223) to an appropriate number of posts (e.g., conductive posts 293) which are disposed in an electrical conductive relationship with the solder balls 222.

Figure 3A:
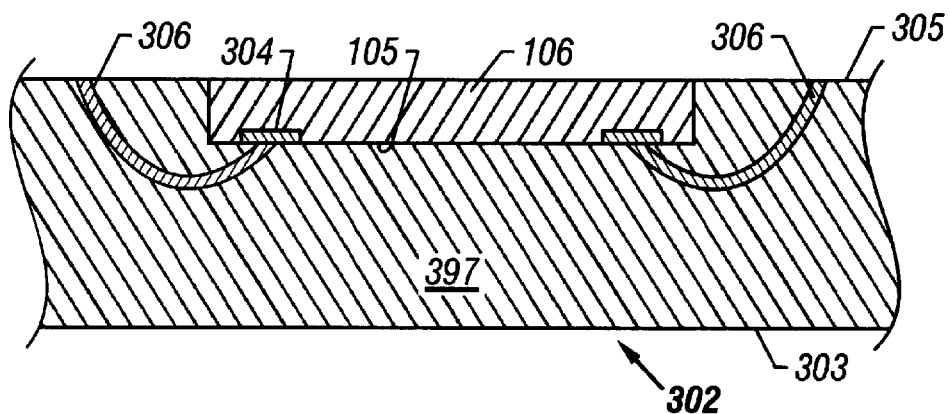
FIG. 3A shows a cross-section of a package with the die in accordance with the teachings of the present invention.
Figure 3B:
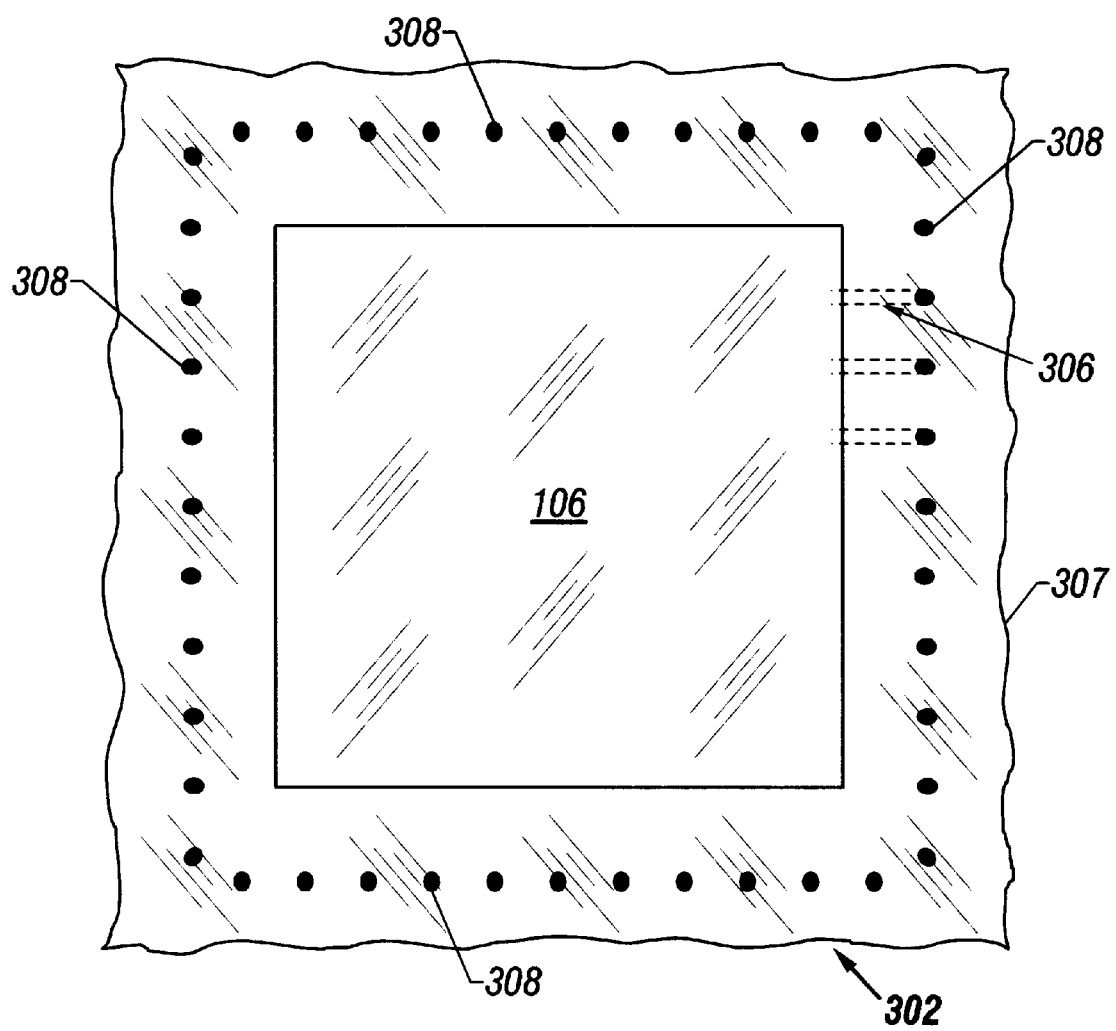
FIG. 3B is a plan view of a package with the die shown in FIG. 3A.
Figure 4:
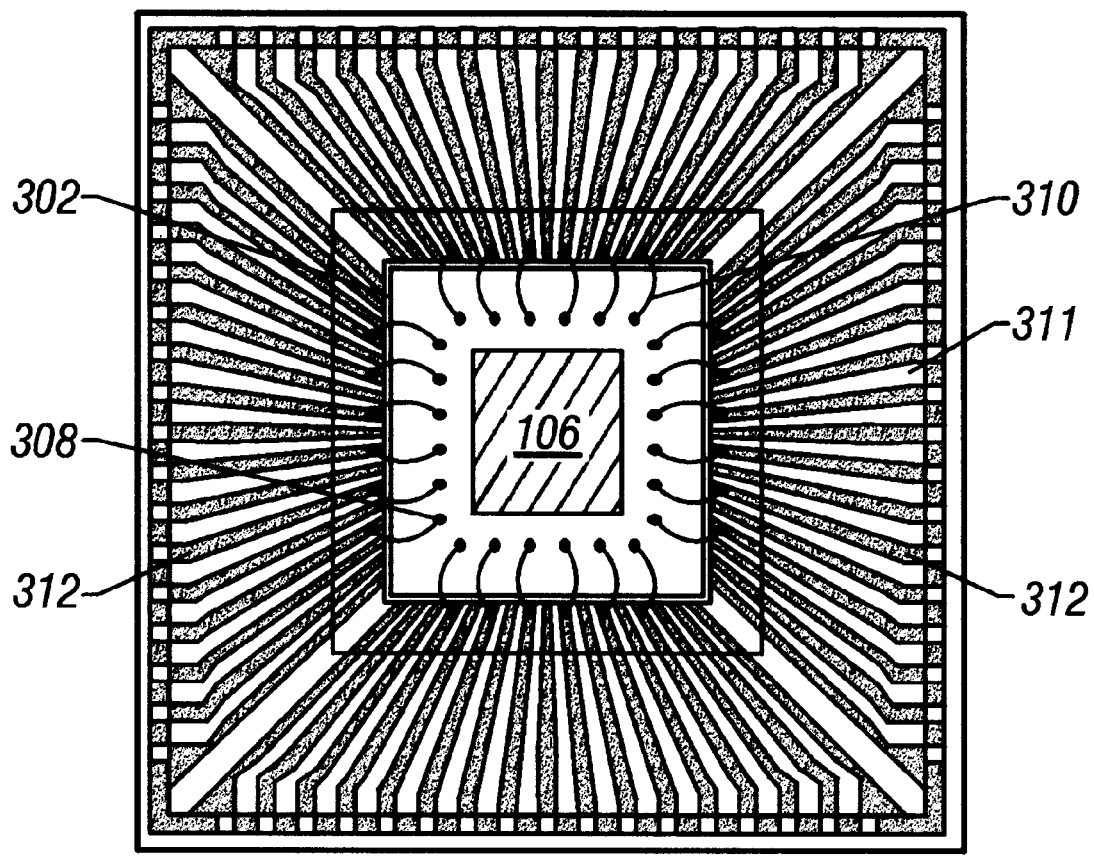
FIG. 4 depicts an exemplary wire-to-wire bonding arrangement in accordance with the teachings of the present invention.
Figure 5A:
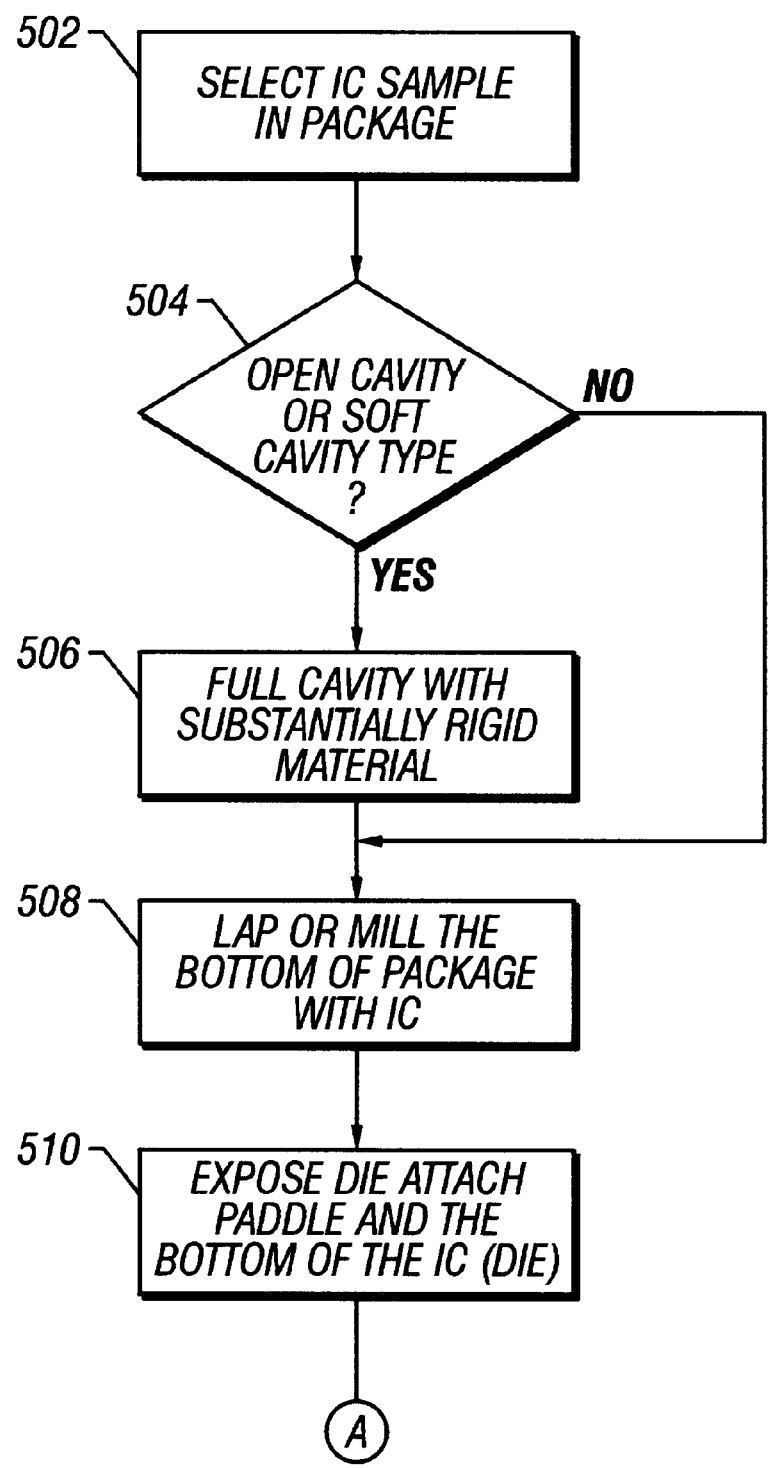
FIGS. 5A and 5B depict a flow chart for an exemplary method of sample preparation for analysis provided in accordance with the teachings of the present invention.
Figure 5B:
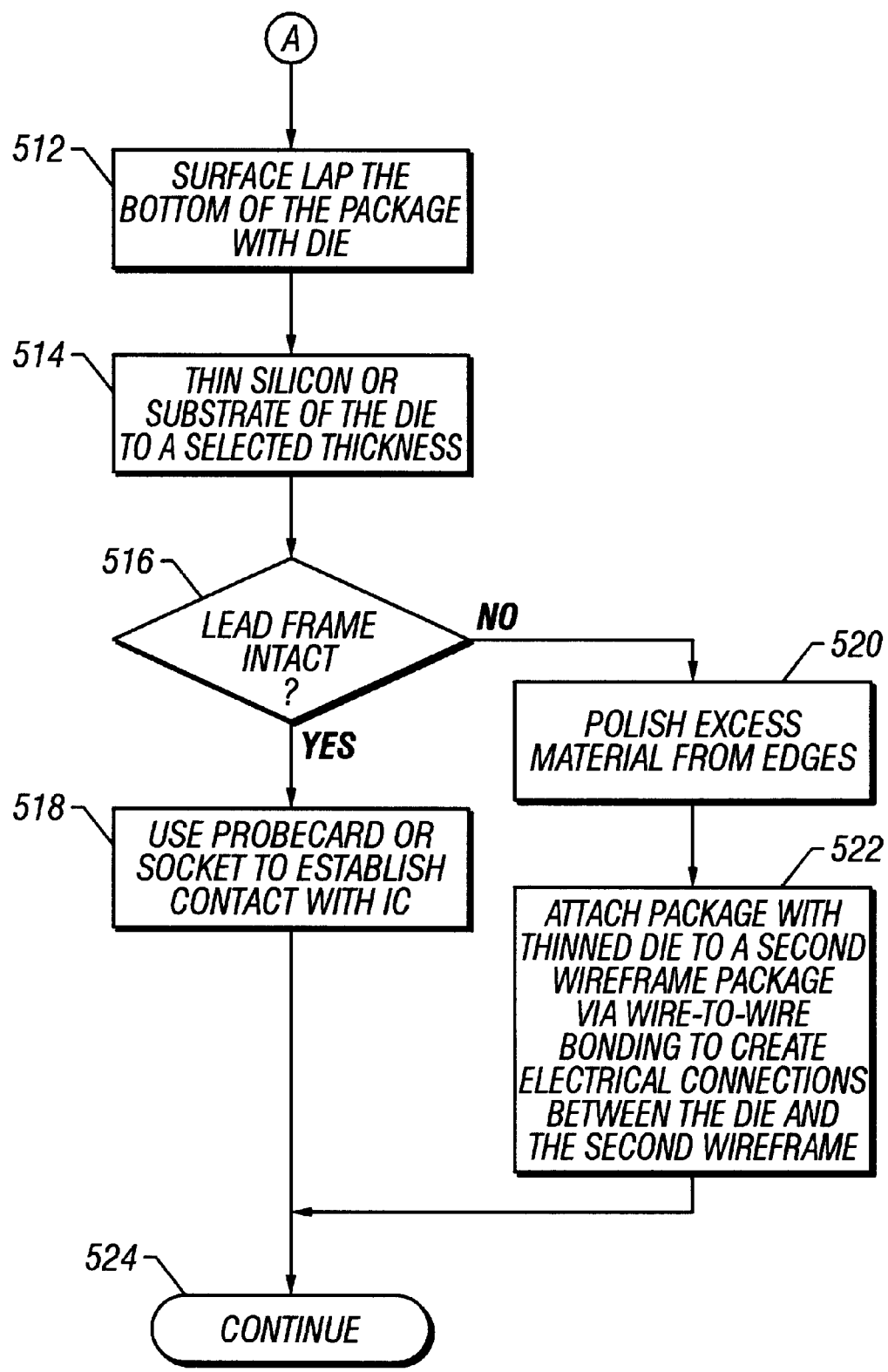

FIGS. 3A and 3B illustrate two views of an intermediate product obtained in the course of sample preparation in accordance with the teachings of the present invention. FIG. 4 depicts a semiconductor sample illustrating an exemplary wire-to-wire bonding arrangement in accordance herewith. FIGS. 5A and 5B depict a flow chart for an exemplary method of sample preparation as per the teachings of the present invention. In the description immediately set forth below, an exemplary embodiment of the method of the present invention will be described in greater detail, taking reference to these FIGS. cumulatively as needed.

FIG. 3A shows a cross-section of an intermediate product 302 which includes a package with the die 106. FIG. 3B is a plan view of the intermediate product 302. After an IC chip or die (e.g., die 106) in package form is selected for sample preparation (step 502), it is determined if the package (e.g., the packages described hereinabove) is of the open cavity or soft cavity type (decision block 504). If so, the die 106 is encapsulated by filling the cavity with a suitable substantially rigid material (e.g., epoxy curable at room temperature) (step 506). On the other hand, if the die 106 is already encapsulated, the step of filling the cavity may be omitted. Those of ordinary skill in the art should realize that filling the cavity with a high temperature epoxy material having an incompatible coefficient of thermal expansion (CTE) with respect to assembly materials may induce mechanical stress due to thermal contraction and thus distort and/or destroy the die when it is thinned. Accordingly, high temperature materials are preferably to be avoided for the purposes of the present invention wherein a variety of packaging compounds such as Thermoset epoxy, blob top epoxy, ceramic, phenolic, etc. may be advantageously used for die encapsulation.

Thereafter, the encapsulated die in package is mounted on a polishing jig using an adhesive material such as hot melt wax, such that the bottom of the package (and the backside of the die) is oriented to an apparatus for removing material by mechanical lapping (i.e., sanding) or milling. That is, the front side 303 of the package is attached to the jig in the exemplary embodiment depicted in FIG. 3A. If needed, a tilt planarization step by using trigonometric techniques may be effectuated in order to substantially planarize the package (i.e., the package and the therein die are rendered substantially parallel to the plane of the polishing jig). A tilt control knob or knobs provided with the polishing jig may be used for planarization.

The bottom of the package with encapsulated die is mechanically lapped or milled (step 508) to expose the die attach paddle and the bottom/backside of the die (step 510). Once the die is exposed, additional package material is removed by surface lapping. That is, the package body, encapsulating material and the exposed semiconductor substrate are preferably surface lapped (step 512). In an exemplary embodiment, favorable results have been obtained by using a 1200 grit sandpaper adhered to the polishing wheel with water only. Comparable results have been obtained by using a 600 grit sandpaper also. The surface lapping step 512 is preferably used until a desired thickness (or, thinness) of the remaining die is achieved, followed by a colloidal silica finish. Preferably, focal depth measurements may be used to determine the amount of remaining substrate, e.g., silicon. For example, a thinness of up to 15 microns, with an accuracy of ±8 microns using a carbide sandpaper and ±4 microns with diamond lapping film, may be obtained.

As shown in the cross-sectional view of the intermediate product 302 in FIG. 3A, wires 306 attached to the bond pads 304 of the semiconductor die 106 remain embedded in the encapsulating material 397 and appear on the finished surface 305 of the intermediate product. The plan view shown in FIG. 3B illustrates the cross-sections 308 of the embedded wires 306. Although not shown in these FIGS., the leadframe of the die 106 may be left intact after the surface removal steps set forth above in some exemplary embodiments, depending upon the package type or configuration.

If it is determined that the leadframe or a portion thereof is left intact after thinning the die to a desired result (decision block 516 in FIG. SB), a probe-card or socket may be contacted thereto for establishing electrical connection or connections to the circuitry of the die (step 518). Also, wires may be bonded to the remaining leadframe for electrical connectivity. Thereafter, the prepared die (i.e, sample) may be used in subsequent analyses, e.g., backside emission microscopy, or other manufacturing/assembly techniques (step 524).

Typically, if the leadframe is gone, the wires 306 which are bonded to the die 106 appear as the cross-sectional spots 308 (hereinafter "wire spots") as exemplified in FIG. 3B. Although mechanical probes may be used to contact these wire spots 308, it should be realized that the pitch therebetween is too irregular for reliable contact because the number of the wires (i.e., the leads or pins of the package) may typically be quite large for such applications. Accordingly, the intermediate product 302 is further processed in accordance with the teachings of the present invention as follows.

Excess material, if any, is removed or trimmed from the edges of the package (i.e., intermediate product 302) so as to preferably achieve substantially smooth edges (step 520). The top surface of the intermediate product 302 (having the polished silicon backside surface) may be thinned, if necessary, without disturbing or breaking the wire loops on the front side of the die. The entire intermediate product 302 now may be treated as a "die", with the wire spots 308 acting as "bond pads".

FIG. 4 shows an exemplary arrangement where the resultant unit/package 302 is attached to a new or second wire/leadframe package carrier 311 having a plurality of conductive lead fingers 312. The attachment is effectuated by employing wire-to-wire bonding between the wire spots 308 of the wires of the die 106 and the fingers 312 of the second wireframe package 311. Reference numeral 310 exemplifies a wire used in the wire-to-wire bonding arrangement described herein.

The new frame package 311 may be coupled to a socket, receptacle, or a loadboard having a pin-out that is a mirror image of the original pin-out of the semiconductor die 106 (pin-out is mirrored because the circuitry of the die is facing down). Also, as those of ordinary skill in the art should readily appreciate, a socket wiring adapter may be used with a test loadboard that is adapted for the original pin-out. After establishing electrical connectivity by the use of appropriate means as set forth above, the resultant semiconductor sample may be used in subsequent analyses (step 524).

Figure 6A:
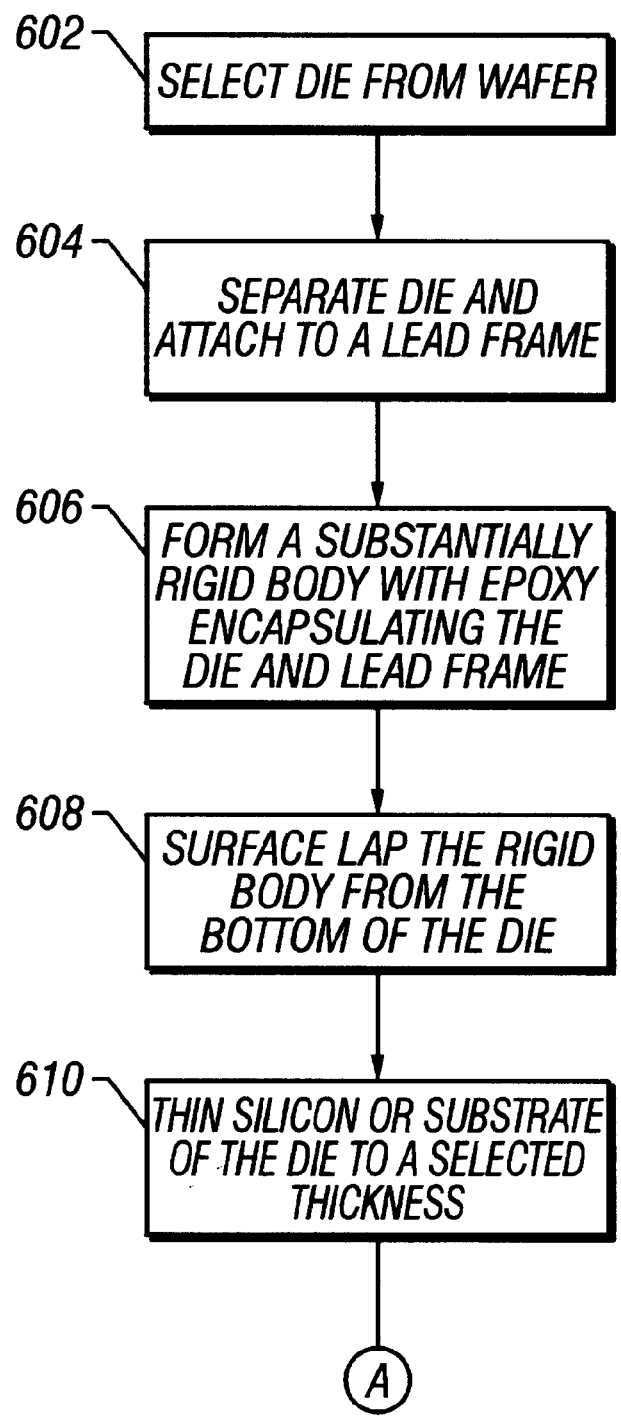
FIGS. 6A and 6B depict a flow chart for another exemplary method of sample preparation for analysis provided in accordance with the teachings of the present invention.
Figure 6B:
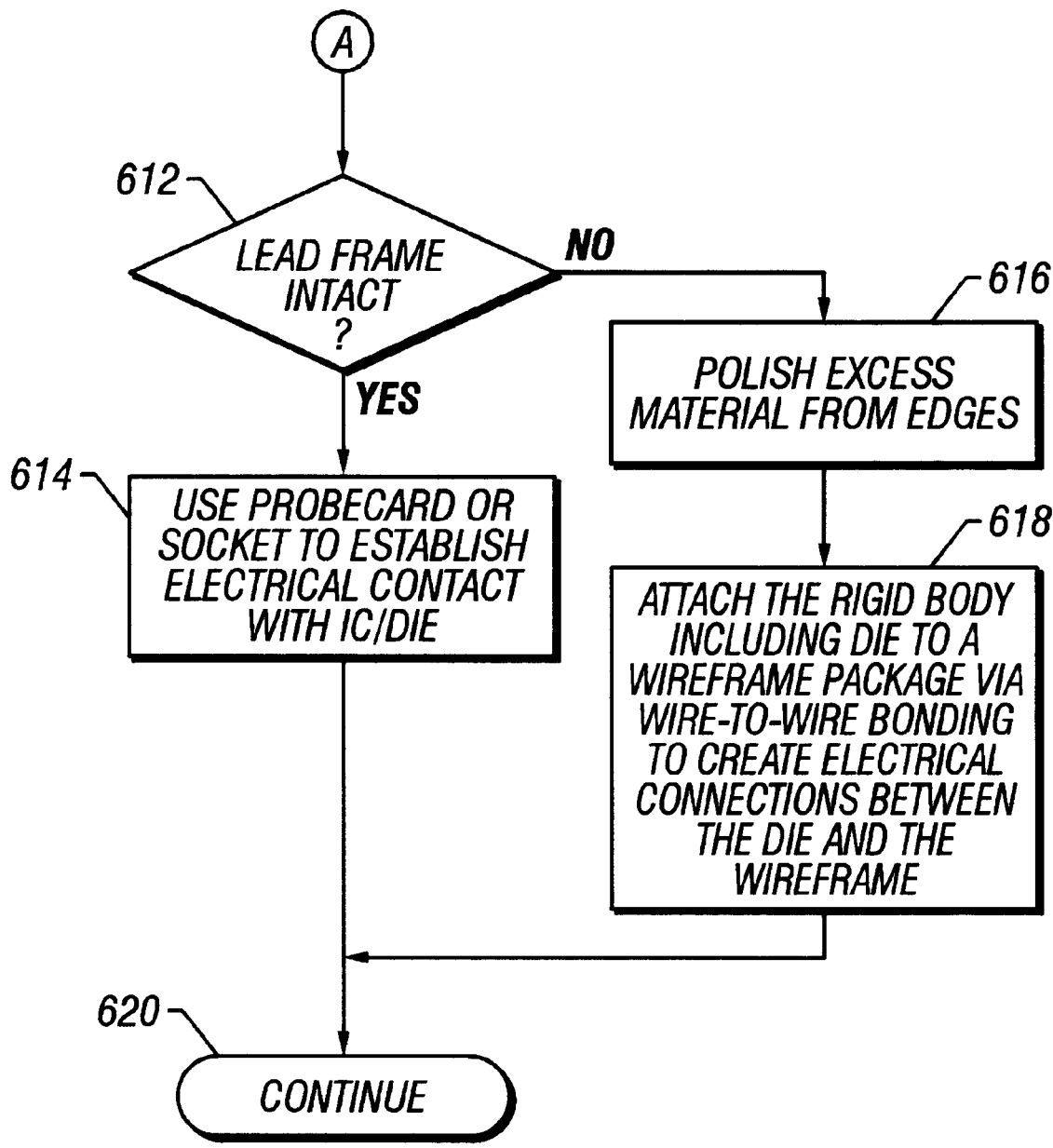

Referring now to FIGS. 6A and 6B, depicted therein is a flow chart for another exemplary method of sample preparation provided in accordance with the teachings of the present invention. In this exemplary method, an unpackaged die (i.e., die in wafer form) is used for preparing a sample. It should be realized upon reference hereto that the steps involved herein are substantially similar to those described hereinabove. Accordingly, only salient features of this exemplary embodiment are set forth hereinbelow.

After selecting a die from a wafer (step 602), it is separated and attached to a leadframe (step 604). A substantially rigid body is formed around the attached die by encapsulating it with a room temperature epoxy or compatible assembly plastic/epoxy with a low CTE (step 608).

Thereafter, a surface of the rigid body that is oriented to the bottom of the semiconductor die is presented for surface removal as described above. Subsequently, the thinned die in the rigid body is wire-to-wire bonded to another leadframe by disposing wires between the wire spots and lead fingers (step 618). Alternatively, the thinned die may be tested in its existing leadframe.

Based on the foregoing, it should be appreciated by those skilled in the art that the present invention provides an innovative solution that overcomes the drawbacks and deficiencies of the existing sample preparation technologies. It should be apparent that the present invention allows traditional fixturing such as test heads or probe stations to be utilized in a normal test mode. No inverted boards cabled to a tester are needed since, at least in one aspect, the thinned die remains in its original package and is polished and re-bonded to a package carrier with the polished backside facing upward. A simple pin reassignment is all that is needed to correct the reverse (or, mirrored) wire sequence after wire-to-wire bonding or wire-to-frame bonding in the new package frame. It should be appreciated that the resultant orientation eliminates many of the problems of the current backside analysis techniques with awkward and/or unwieldy sample orientations, because of the upward facing of the polished surface of samples.

Also, because of the upward orientation of the polished backside silicon, test equipment can be used in conjunction with analytical tools such as an emission microscope or focused ion beam (FIB) equipment. Moreover, the low profiles of samples prepared in accordance with the teachings of the present invention allow various immersion lenses (oil, water, etc.) to be advantageously employed in emission microscopy. Furthermore, because substantially thin silicon samples can be obtained from the practice of the present invention, light sources of shorter wavelength may be used in analytical techniques with substantially improved optical resolution.

It should further be appreciated that various surface probe and imaging techniques become viable from the backside of silicon due to the flat profiles of samples prepared in accordance herewith such as: liquid crystal analyses, fluorescent microthermographic imaging (FMI), FIB techniques, OBIC, LIVA and TIVA analyses, etc.

In addition, because samples of semiconductor die-in-wafer-form can also be prepared in accordance herewith, the teachings of the present invention may be advantageously employed in yield analysis as well. The exemplary preparation techniques described herein may also be used with advanced packages such as the BGA packages, CSPs, et cetera, in addition to all known package types, for example, Pin Grid Array (PGA) packages, Plastic Leadless Chip Carriers (PLCCs), all varieties of Dual In-line Packages (DIPs) and Flip Chips, Small Outline ICs (SOICs), Plastic Quad Flat Packs (PQFPs), etc.

Additionally, it should be apparent to one of ordinary skill in the art upon reference hereto that the teachings ofthe present invention may be advantageously used in conjunction with assembly processing of Multi-Chip Modules (MCMs) where two or more chips are thinned and stacked together. The wire-to-wire bonding technique may then be employed advantageously for providing electrical contract between the chips. For example, a first semiconductor chip and a second semiconductor chip may be prepared separately using the steps set forth in FIGS. 6A and 6B. Instead of using a probe-card, socket, or another wireframe, the prepared chips may then be wire-bonded together, with or without lead frame/s being intact.

Further, it is believed that the operation and construction of the present invention will be apparent from the foregoing Detailed Description. While the method and system shown and described have been characterized as being preferred, it should be readily understood that various changes and modifications could be made therein without departing from the scope of the present invention as set forth in the following claims.

What is claimed is:

1. A method of preparing a semiconductor sample from a package with a semiconductor die disposed therein, said package having a cavity bounded by a top and a bottom, said semiconductor die being attached to a leadframe through a die paddle and a plurality of wires bonded therebetween, wherein said cavity of said package is filled with a substantially rigid material, said method comprising the steps of:

removing a portion of said package, starting from said bottom, including said substantially rigid material;

exposing said die attach paddle and the backside of said semiconductor die;

removing an additional portion of said package including said substantially rigid material and thinning said semiconductor die to a selected thickness;

if said leadframe is sacrificed in at least one of said step of removing said portion and said step of removing said additional portion, placing said package with said die in a second package with a wireframe having a plurality of lead fingers;

bonding exposed wire spots on the backside of said die to said plurality of lead fingers; and if said leadframe is not sacrificed, contacting said leadframe or a remaining portion thereof to a suitable fixture.

2. The method of preparing a semiconductor sample as set forth in claim 1, wherein said step of removing a portion of said package comprises mechanical lapping.

3. The method of preparing a semiconductor sample as set forth in claim 1, wherein said step of removing a portion of said package comprises milling.

4. The method of preparing a semiconductor sample as set forth in claim 1, further comprising the steps of:

mounting said package with said die on a polishing jig prior to removing a portion of said package; and planarizing said polishing jig with respect to said bottom of said package.

5. The method of preparing a semiconductor sample as set forth in claim 1, wherein said step of removing an additional portion of said package including said substantially rigid material is effectuated by a sandpaper of approximately 600 grit to 1200 grit mounted on a polishing wheel.

6. The method of preparing a semiconductor sample as set forth in claim 5, further comprising the step of:

finishing with a colloidal silica polish after said step of removing an additional portion of said package.

7. The method of preparing a semiconductor sample as set forth in claim 1, wherein said second package comprises a ceramic pin grid array.

8. The method of preparing a semiconductor sample as set forth in claim 1, wherein said selected thickness is approximately 15 to 50 microns.

9. The method of preparing a semiconductor sample as set forth in claim 1, wherein said suitable fixture comprises a wireframe.

10. The method of preparing a semiconductor sample as set forth in claim 1, wherein said suitable fixture comprises a probe-card.

11. A method of preparing a semiconductor sample from a package with a semiconductor die disposed therein, said package having a cavity bounded by a top and a bottom, said semiconductor die being attached to a leadframe through a die paddle and a plurality of wires bonded therebetween, wherein said package is of the open cavity type or the soft cavity type, said method comprising the steps of:

filling said cavity with a substantially rigid material;

removing a portion of said package including said substantially rigid material, starting from said bottom;

exposing said die attach paddle and the backside of said semiconductor die;

removing an additional portion of said package including said substantially rigid material and thinning said semiconductor die to a selected thickness;

if said leadframe is sacrificed in at least one of said step of removing said portion and said step of removing said additional portion, placing said package with said die in a second package with a wireframe having a plurality of lead fingers;

bonding exposed wire spots on the backside of said die to said plurality of lead fingers; and if said leadframe is not sacrificed, contacting said leadframe or a remaining portion thereof to a suitable fixture.

12. The method of preparing a semiconductor sample as set forth in claim 11, wherein said substantially rigid material comprises a room temperature epoxy.

13. The method of preparing a semiconductor sample as set forth in claim 11, wherein said substantially rigid material comprises a Thermoset epoxy.

14. The method of preparing a semiconductor sample as set forth in claim 11, wherein said substantially rigid material comprises a blob top epoxy.

15. The method of preparing a semiconductor sample as set forth in claim 11, wherein said step of removing a portion of said package comprises mechanical lapping.

16. The method of preparing a semiconductor sample as set forth in claim 11, wherein said step of removing a portion of said package comprises milling.

17. The method of preparing a semiconductor sample as set forth in claim 11, further comprising the steps of:

mounting said package with said die on a polishing jig prior to removing a portion of said package; and planarizing said polishingjig with respect to said bottom of said package.

18. The method of preparing a semiconductor sample as set forth in claim 11, wherein said step of removing an additional portion of said package including said substantially rigid material is effectuated by a sandpaper of approximately 600 grit to 1200 grit mounted on a polishing wheel.

19. The method of preparing a semiconductor sample as set forth in claim 18, further comprising the step of finishing with a colloidal silica polish after said step of removing an additional portion of said package.

20. The method of preparing a semiconductor sample as set forth in claim 18, wherein said second package comprises a ceramic pin grid array.

21. The method of preparing a semiconductor sample as set forth in claim 11, wherein said selected thickness is approximately 15 to 50 microns.

22. The method of preparing a semiconductor sample as set forth in claim 11, wherein said suitable fixture comprises a wireframe.

23. The method of preparing a semiconductor sample as set forth in claim 11, wherein said suitable fixture comprises a probe-card.

24. A method of preparing a semiconductor sample from a die disposed in a wafer, comprising the steps of:

separating said die from said wafer and attaching said die to a leadframe through a die attach paddle and a plurality of wires bonded therebetween;

forming a substantially rigid body around said die by encapsulating said die, said leadframe and said wires in a substantially rigid material, said substantially rigid body having a bottom surface oriented to a bottom surface of said die;

removing a portion of said substantially rigid body, starting its bottom surface;

exposing said die attach paddle and said bottom of said semiconductor die;

removing an additional portion of said substantially rigid body and thinning said die to a selected thickness;

if said leadframe is sacrificed in at least one of said step of removing said portion and said step of removing said additional portion, placing said substantially rigid body with said die in a package with a wireframe having a plurality of lead fingers;

bonding exposed wire spots on said die to said plurality of lead fingers; and if said leadframe is not sacrificed, contacting said leadframe or a remaining portion thereof to a suitable fixture.

25. The method of preparing a semiconductor sample as set forth in claim 24, wherein said step of removing a portion of said package comprises mechanical lapping.

26. The method of preparing a semiconductor sample as set forth in claim 24, wherein said step of removing a portion of said package comprises milling.

27. The method of preparing a semiconductor sample as set forth in claim 24, further comprising the steps of:

mounting said substantially rigid body with said die on a polishing jig prior to removing a portion thereof; and planarizing said polishing jig with respect to said bottom of said substantially rigid body.

28. The method of preparing a semiconductor sample as set forth in claim 24, wherein said step of removing an additional portion of said substantially rigid body is effectuated by a sandpaper of approximately 600 grit to 1200 grit mounted on a polishing wheel.

29. The method of preparing a semiconductor sample as set forth in claim 28, further comprising the step of:

finishing with a colloidal silica polish after said step of removing an additional portion of said substantially rigid body.

30. The method of preparing a semiconductor sample as set forth in claim 24, wherein said package comprises a ceramic pin grid array.

31. The method of preparing a semiconductor sample as set forth in claim 24, wherein said selected thickness is approximately 15 to 50 microns.

32. The method of preparing a semiconductor sample as set forth in claim 24, wherein said suitable fixture comprises a wireframe.

33. The method of preparing a semiconductor sample as set forth in claim 24, wherein said suitable fixture comprises a probe-card.

34. The method of preparing a semiconductor sample as set forth in claim 24, wherein said substantially rigid material comprises a room temperature epoxy.

35. The method of preparing a semiconductor sample as set forth in claim 24, wherein said substantially rigid material comprises a Thermoset epoxy.

36. The method of preparing a semiconductor sample as set forth in claim 24, wherein said substantially rigid material comprises a blobtopepoxy.

37. A sample preparation system for preparing a semiconductor sample from a first package containing a semiconductor die wherein said semiconductor die is bonded to a leadframe with a plurality of wires, said system comprising:

means for mounting said first package on a polishing jig such that the backside of said semiconductor die is facing a polishing wheel;

means for removing a portion of said first package and said semiconductor die until a selected thickness of the said die is obtained; and means for bonding wire spots exposed on the backside of said die to a plurality of lead fingers of a second package.

38. The sample preparation system as set forth in claim 37, wherein said second package comprises a ceramic pin grid array package.

39. The sample preparation system as set forth in claim 37, further comprising means for planarizing said polishing jig with respect to said semiconductor die.

40. The sample preparation system as set forth in claim 37, wherein said selected thickness is about 15 to 50 microns.

* * * * *